(12) United States Patent
Park et al.

(10) Patent No.: US 11,617,896 B2
(45) Date of Patent: Apr. 4, 2023

(54) MEDICAL WOUND HEALING ACCELERATOR AND OSTEOMYELITIS TREATMENT DEVICE

(71) Applicant: KOREA UNIVERSITY RESEARCH AND BUSINESS FOUNDATION, Seoul (KR)

(72) Inventors: Jong Woong Park, Seoul (KR); Tae Jin Song, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 173 days.

(21) Appl. No.: 15/743,504

(22) PCT Filed: Jun. 3, 2016

(86) PCT No.: PCT/KR2016/005890
§ 371 (c)(1),
(2) Date: Jan. 10, 2018

(87) PCT Pub. No.: WO2017/010685
PCT Pub. Date: Jan. 19, 2017

(65) Prior Publication Data
US 2018/0200533 A1    Jul. 19, 2018

(30) Foreign Application Priority Data

Jul. 10, 2015  (KR) .......................... 10-2015-0098381
Mar. 10, 2016  (KR) .......................... 10-2016-0029041

(51) Int. Cl.
*A61N 5/00*     (2006.01)
*A61N 5/06*     (2006.01)
(Continued)

(52) U.S. Cl.
CPC ............ *A61N 5/0616* (2013.01); *A61L 27/14* (2013.01); *A61L 27/50* (2013.01); *A61L 27/54* (2013.01);
(Continued)

(58) Field of Classification Search
CPC .. A61N 5/0613; A61N 1/36021; A61B 17/56; A61B 17/58; A61B 17/08; A61B 90/03; F16B 7/04
(Continued)

(56) References Cited

U.S. PATENT DOCUMENTS 7,513,906 B2     4/2009  Passy et al.
2006/0271131 A1*  11/2006  Passy ................... A61N 5/0613
                                                          607/88

(Continued)

FOREIGN PATENT DOCUMENTS

JP    2015-129128    7/2015
KR    2002-0014084   2/2002

*Primary Examiner* — Rex R Holmes
*Assistant Examiner* — Sana Sahand
(74) *Attorney, Agent, or Firm* — Duane Morris LLP; Gregory M. Lefkowitz; Brandon A. Chan (57) ABSTRACT

A medical wound healing accelerator having a body that is removably attached on a fixing pin, of an external fixator for fractures, that is insertable into a bone through skin is provided. The device can further include a plurality of light source units arranged on one surface of the body to emit light and provide a beneficial effect to the wound, and a controller electrically connected to the light source units. An osteomyelitis treatment device having an insert that is insertable into an osteomyelitis part in a human body, and a plurality of light-emitting members provided to the insert to emit light is also provided. The plurality of light-emitting (Continued)

members can be spaced apart from each other, and a part of the insert can be cut or bent to correspond to the shape of the osteomyelitis part.

7 Claims, 9 Drawing Sheets (51) Int. Cl.
  *A61L 27/50*    (2006.01)
  *A61L 27/54*    (2006.01)
  *A61L 31/14*    (2006.01)
  *A61L 31/16*    (2006.01)
  *A61L 31/04*    (2006.01)
  *A61L 27/14*    (2006.01)
  *A61B 17/60*    (2006.01)
  *A61B 5/00*    (2006.01)
  *A61B 17/62*    (2006.01)

(52) U.S. Cl.
  CPC ............... *A61L 31/04* (2013.01); *A61L 31/14* (2013.01); *A61L 31/16* (2013.01); *A61B 5/445* (2013.01); *A61B 17/60* (2013.01); *A61B 17/62* (2013.01); *A61L 2300/402* (2013.01); *A61L 2300/404* (2013.01); *A61N 2005/0626* (2013.01); *A61N 2005/0633* (2013.01); *A61N 2005/0643* (2013.01); *A61N 2005/0652* (2013.01); *A61N 2005/0663* (2013.01)

(58) Field of Classification Search
  USPC ..................................................... 607/88, 94
  See application file for complete search history.

(56) References Cited

U.S. PATENT DOCUMENTS

| | | |
|---|---|---|
| 2007/0005071 A1 | 1/2007 | Kucklick |
| 2007/0129776 A1* | 6/2007 | Robins ................ A61N 5/0613 607/88 |
| 2008/0221652 A1 | 9/2008 | DiMauro et al. |
| 2010/0030219 A1* | 2/2010 | Lerner ................. A61B 90/11 606/87 |
| 2010/0145357 A1* | 6/2010 | Lane .................... A61N 1/0539 606/129 |
| 2010/0256541 A1* | 10/2010 | Pryor ................... A61N 5/0613 602/2 |
| 2011/0221140 A1* | 9/2011 | Nakagawa ........... F16J 15/3456 277/412 |
| 2012/0219354 A1* | 8/2012 | Bauer .................... F16B 7/048 403/187 |
| 2013/0131762 A1* | 5/2013 | Oversluizen ......... A61N 5/0616 607/90 |
| 2013/0197317 A1* | 8/2013 | Daniel ................ A61B 1/0684 600/249 |
| 2014/0211459 A1* | 7/2014 | Toner ..................... E04H 12/32 362/183 |
| 2014/0211470 A1* | 7/2014 | Kinnune ................ F21V 29/74 362/249.02 |

* cited by examiner

MEDICAL WOUND HEALING ACCELERATOR AND OSTEOMYELITIS TREATMENT DEVICE

CROSS-REFERENCE TO RELATED APPLICATIONS

This application is a § 371 national stage entry of International Application No. PCT/KR2016/005890, filed on Jun. 3, 2016, which claims priority to South Korean Patent Application No. 10-2015-0098381, filed on Jul. 10, 2015, and South Korean Patent Application No. 10-2016-0029041, filed on Mar. 10, 2016, the entire contents of which are incorporated herein by reference.

TECHNICAL FIELD

The present disclosure relates to a medical wound healing accelerator, and more particularly, to a medical wound healing accelerator that provides beneficial effects for wound healing by light irradiation on a wound site using a light emitting diode (LED) as a light source.

Further, the present disclosure relates to an osteomyelitis treatment device, and more particularly, an osteomyelitis treatment device for treating osteomyelitis using light with antibacterial action.

BACKGROUND ART

In general, blue light of 400 nm to 470 nm wavelength produced using a light emitting diode (LED) as a light source is known as providing antibacterial effects and beneficial effects for wound healing acceleration.

The blue light using an LED as a light source provides the above-mentioned beneficial effects by irradiation of blue light of 400 nm to 470 nm wavelength on the skin, and its use is gradually expanding in various medical fields, and for example, it is used in the treatment of many types of skin diseases such as acne.

Recently, a portable blue light apparatus using an LED as a light source was developed and is commercially available for a patient suffering from a skin disease to conveniently use at a desired place and time without the need to go to hospital.

The above-mentioned blue light apparatus using an LED as a light source allows a patient to treat a skin disease in person by direct irradiation of blue light on the skin of the face after the patient holds the blue light apparatus, and thus has the limited use and purpose.

For example, in the case of a patient using an external fixator for fracture for fixing and correcting fractured and displaced parts of the bone outside to restore to the original condition, the skin is infected by fixing pins inserted into the bone through the skin, and in severe cases, osteomyelitis often develops.

When blue light irradiation is applied to the skin of the patient using the external fixator for fracture through the blue light apparatus to prevent the skin infection, there may be limitations in applying blue light irradiation on the skin due to the external fixator for fracture installed along the outer side of the arm or leg.

In particular, the external fixator for fracture includes a plurality of pins inserted through the skin depending on the patient's condition, and it is impossible to apply blue light irradiation over a wide area using only one apparatus in response to each pin, and to solve this, a plurality of identical apparatuses is required.

Additionally, because the patient with fractures has limited physical activities according to the properties, the patient cannot treat himself/herself through the blue light apparatus, and when the patient receives assistance from another person, the patient cannot receive treatment at the desired time, and has only limited treatment, not continuous and consecutive treatment, because the patient has to receive assistance from another person.

Accordingly, for the patient with fractures using the external fixator for fracture to use the above-mentioned apparatus for blue light irradiation using an LED as a light source, an apparatus having completely different configuration is required.

Meanwhile, in general, after chronic osteomyelitis or artificial joints, in the event of bone infection, intravascular injection or oral antibiotic administration has insufficient antibiotic concentration at a local site, and to maintain the local antibiotic concentration, antibiotic-containing cement is inserted. In this instance, the cement has various shapes such as beads and artificial joints depending on the purpose.

However, the antibiotic release of the antibiotic cement only lasts about 2-3 days after surgery, and afterwards, the cement may act as a foreign body in the human body. Additionally, systemic effects of the antibiotic cement result in risks of systemic adverse effects such as a kidney failure.

To address this issue, various antibiotic cements have been developed, and for example, KR 2000-0047171 filed on Aug. 16, 2000 discloses 'antibiotic-loaded cement spacer manufacturing method'.

The disclosure described in the background art part is provided for a better understanding of the background of the invention, and may include content other than the conventional art already known to those skilled in the art.

DISCLOSURE

Technical Problem

Embodiments of the present disclosure are directed to providing a medical wound healing accelerator that is installed on a fixing pin of an external fixator for fracture inserted into the bone through the skin to irradiate beneficial light for treatment onto regions near the skin through which the fixing pin penetrates.

Additionally, embodiments of the present disclosure are directed to providing an osteomyelitis treatment device in which an insert is made of a polymer material and is easy to fold or cut to conform to the shape of an osteomyelitis site.

Additionally, embodiments of the present disclosure are directed to providing an osteomyelitis treatment device in which a light-emitting member is connected to a battery and a charging coil, allowing wireless charging of the battery, to emit light of the same intensity from the light-emitting member for a desired period, thereby obtaining the same antibacterial action by the light-emitting member.

Additionally, embodiments of the present disclosure are directed to providing an osteomyelitis treatment device that effectively prevents or treats osteomyelitis by the light-emitting member for blue light with antibacterial action, and allows local site irradiation in the human body by the light-emitting member, thereby preventing systemic complications.

Additionally, embodiments of the present disclosure are directed to providing an osteomyelitis treatment device in which the insert is additionally provided with a capsule, thereby obtaining more effective antibacterial effects through individual antibacterial action of the light-emitting member and the capsule or antibacterial action by interaction between the capsule and the light-emitting member.

Additionally, embodiments of the present disclosure are directed to providing an osteomyelitis treatment device in which silicon coating of a transparent material harmless for the human body is applied to the insert, thereby minimizing local site foreign body reaction in the human body and preventing electrical complications.

Additionally, embodiments of the present disclosure are directed to providing an osteomyelitis treatment device in which the insert is easily fabricated to conform to the shape of an osteomyelitis site or joint of a patient or with a customized shape and size desired by the patient using 3D printing fabrication technology.

Additionally, embodiments of the present disclosure are directed to providing an osteomyelitis treatment device that can be used to treat infection in osteomyelitis of tibia or artificial joint inserted sites of knees as well as deep soft tissue infection, osteomyelitis, and infection in artificial joint inserted sites of hip joints, shoulder joints and knee joints over all parts of the body, and can be used to treat even animals.

Technical Solution

A medical wound healing accelerator according to an embodiment of the present disclosure may include a body attachably/detachably installed on a fixing pin of an external fixator for fracture which is inserted into a bone through a skin, a plurality of light source units arranged on one side surface of the body to irradiate a beneficial light to a wound onto the skin, and a controller electrically connected to the light source units to control operation of the light source units.

Additionally, in the medical wound healing accelerator according to an embodiment of the present disclosure, the body may be divided into a first body and a second body, and the first and second bodies may be hinge coupled to each other on one side and fastened to each other through a fastener provided on the other side.

Additionally, in the medical wound healing accelerator according to an embodiment of the present disclosure, one side of the fastener may be rotatably coupled to an outer circumferential surface of the first body, and a front end of the other side may be coupled to an outer circumferential surface of the second body by rotation, so that the first body and the second body may be fastened to each other.

Additionally, in the medical wound healing accelerator according to an embodiment of the present disclosure, the fastener may include a coupling end rotatably coupled to the outer circumferential surface of the first body, a fastening end fastened to the outer circumferential surface of the second body, and a connecting end connecting the coupling end to the fastening end.

Additionally, in the medical wound healing accelerator according to an embodiment of the present disclosure, the light source unit may irradiate blue light of 300 nm to 500 nm wavelength using a light emitting diode (LED) as a light source.

Additionally, the medical wound healing accelerator according to an embodiment of the present disclosure may further include an active member installed in a through hole of the body through which the fixing pin goes, to actively respond to a diameter of the fixing pin.

Additionally, in the medical wound healing accelerator according to an embodiment of the present disclosure, the active member may include an active body having an active hole through which the fixing pin goes at a center, and a coupling flange which extends outward along an outer circumferential surface of the active body and is inserted into a coupling hole formed along an inner circumferential surface of the through hole formed in the body.

Additionally, in the medical wound healing accelerator according to an embodiment of the present disclosure, the active member may be made of a synthetic resin material having elasticity per se.

Additionally, the medical wound healing accelerator according to an embodiment of the present disclosure may further include at least one light receiving sensor installed on the body and electrically connected to the controller, wherein the light receiving sensor may detect a skin color changing depending on a degree of inflammation and changes output of light irradiated from the light source unit.

Meanwhile, an osteomyelitis treatment device according to an embodiment of the present disclosure may include an insert which is insertable into an osteomyelitis site in a body, and a plurality of light-emitting members provided in the insert to emit light, wherein the insert may have a plurality of receiving blocks in which the plurality of light-emitting members is received, and a connected part of the plurality receiving blocks may be cuttable or foldable to conform to a shape of the osteomyelitis site.

Additionally, the osteomyelitis treatment device according to an embodiment of the present disclosure may further include a power supply member including a battery for supplying power to the plurality of light-emitting members and a wireless charging member for wirelessly charging the battery by an electromagnetic induction method.

Additionally, in the osteomyelitis treatment device according to an embodiment of the present disclosure, the wireless charging member may include an external charger placed outside, and a charging coil which generates an induced current by an electromagnetic induction method with the external charger, and the charging coil may be placed adjacent to the battery.

Additionally, in the osteomyelitis treatment device according to an embodiment of the present disclosure, the power supply member may include a first wire which supplies current from the battery to the insert, and a second wire connected between the plurality of light-emitting members to transmit the current supplied from the first wire to the plurality of light-emitting members.

Additionally, in the osteomyelitis treatment device according to an embodiment of the present disclosure, the second wire may be placed in a connected part of the plurality of receiving blocks, and the second wire may be folded or cut by folding or cutting of the insert.

Additionally, the osteomyelitis treatment device according to an embodiment of the present disclosure may further include a controller for controlling operation of the plurality of light-emitting members, wherein the controller may be connected to the insert and inserted into the body.

Additionally, in the osteomyelitis treatment device according to an embodiment of the present disclosure, the insert may be made of a flexible polymer material and coated with silicon, and the plurality of light-emitting members may include an LED or a laser which emits blue light.

Additionally, the osteomyelitis treatment device according to an embodiment of the present disclosure may further include a capsule provided in the insert, the capsule in which an antibacterial material or a pain mitigation material is received, wherein breakage of the capsule may be controlled by the control of light emitted from the light-emitting member.

Further, an osteomyelitis treatment device according to an embodiment of the present disclosure includes an insert which is insertable into an osteomyelitis site in a body, a light-emitting member provided in the insert to emit light, and a capsule provided in the insert, the capsule in which an antibacterial material or a pain mitigation material is received, wherein a battery which supplies power the light-emitting member may be placed in the body, and the battery may be wirelessly charged by an external charger placed outside.

Additionally, in the osteomyelitis treatment device according to an embodiment of the present disclosure, the capsule may be breakable by light emitted from the light-emitting member or an external environment around the osteomyelitis site, and the external environment around the osteomyelitis site may include temperature, pressure or humidity.

Additionally, in the osteomyelitis treatment device according to an embodiment of the present disclosure, a plurality of light-emitting members may be inserted into the insert, the plurality of light-emitting members may be spaced apart from each other along a lengthwise direction of the insert, and an area between the plurality of light-emitting members spaced apart in the insert may be cuttable or foldable to conform to a shape of the osteomyelitis site.

Additionally, in the osteomyelitis treatment device according to an embodiment of the present disclosure, the insert may be made of a polymer material and fabricated by 3D printing to conform to a shape of a joint, and the light-emitting member may be inserted into the insert fabricated by the 3D printing.

Advantageous Effects

The embodiments of the present disclosure are installed on the fixing pin which is inserted into the bone through the skin to irradiate blue light which provides beneficial effects for the skin, thereby preventing the skin from being infected by the fixing pin penetrating the skin, and accelerating the healing of a wound occurring when the fixing pin penetrates the skin.

Additionally, the embodiments of the present disclosure are installed on the fixing pin of the external fixator for fracture, thereby easily irradiating blue light onto the skin without being interrupted by each frame of the external fixator for fracture while in use, and accurately irradiating blue light onto a wound site through which the fixing pin goes.

Additionally, the embodiments of the present disclosure are installed on the fixing pin of the external fixator for fracture, to allow a patient having limited activities by the external fixator for fracture to treat himself/herself without assistance of another person, thereby achieving continuous and consecutive treatment and reducing the number of disinfection operations performed on the wound site.

Meanwhile, according to the embodiments of the present disclosure, the insert is made of a polymer material and is easy to fold or cut to conform to the shape of the osteomyelitis site.

Additionally, according to the embodiments of the present disclosure, the light-emitting member is connected to the battery and the charging coil, allowing wireless charging of the battery, to emit light of the same intensity from the light-emitting member for a desired period, thereby obtaining the same antibacterial action by the light-emitting member.

Additionally, the embodiments of the present disclosure may effectively prevent or treat osteomyelitis by the light-emitting member for blue light with antibacterial action, and allow local site irradiation in the human body by the light-emitting member, thereby preventing systemic complications.

Additionally, according to the embodiments of the present disclosure, the insert is additionally provided with the capsule, thereby obtaining more effective antibacterial effect through individual antibacterial action of the light-emitting member and the capsule or antibacterial action by interaction between the capsule and the light-emitting member.

Additionally, according to the embodiments of the present disclosure, silicon coating harmless for the human body is applied to the insert, thereby minimizing local site foreign body reaction in the human body and preventing electrical complications.

Additionally, according to the embodiments of the present disclosure, the insert may be easily fabricated to conform to the shape of the patient's osteomyelitis site or joint or with a customized shape and size desired by the patient using 3D printing fabrication technology.

Additionally, the embodiments of the present disclosure can be used to treat osteomyelitis of tibia as well as deep soft tissue infection, osteomyelitis, and infection in artificial joint inserted sites of all parts of the body including the knees, such as hip joints, shoulder joints and knee joints, and can be used to treat even animals.

The detailed description of the embodiments of the present disclosure will explicitly or implicitly disclose other effects that can be obtained or are expected by the embodiments of the present disclosure. That is, a variety of expected effects according to the embodiments of the present disclosure will be disclosed in the detailed description as below.

BEST MODE

Hereinafter, the embodiments of the present disclosure will be described in detail with reference to the accompanying drawings.

Rather, the size and thickness of each element shown in the drawings are arbitrarily represented for convenience of description, and the present disclosure is not necessarily limited to illustration shown in the drawings, and the thickness is exaggerated to clearly depict many parts and areas.

Rather, to clearly describe the embodiments of the present disclosure, irrelevant description is omitted herein, and throughout the specification, the same or similar elements are given the same reference numerals.

In the following description, name classification of the elements into "first", "second" and the like may be used to distinguish the elements with the same name, and are not necessarily limited to the order.

As used in this specification, "comprising" specifies the presence of stated elements, and does not preclude the presence or addition of other elements unless the context clearly indicates otherwise.

A medical wound healing accelerator according to the embodiments of the present disclosure provides is installed on a fixing pin 2 of an external fixator 1 for fracture inserted into a bone through skin F, to irradiate beneficial light for treatment onto regions near the skin F through which the fixing pin 2 penetrates, thereby providing antibacterial effects and beneficial effects for wound healing acceleration.

Here, the external fixator 1 for fracture refers to a device that fixes and corrects a fractured and displaced part of the bone outside to restore to the original condition.

The external fixator 1 for fracture described in the embodiments of the present disclosure includes all types of external fixators 1 for fracture, including a type of external fixator for fracture installed encircling the fractured part and a type of external fixator for fracture installed in a plate shape.

The external fixator 1 for fracture is well known technology commonly used in the art, and its detailed description is omitted herein.

Figure 1:
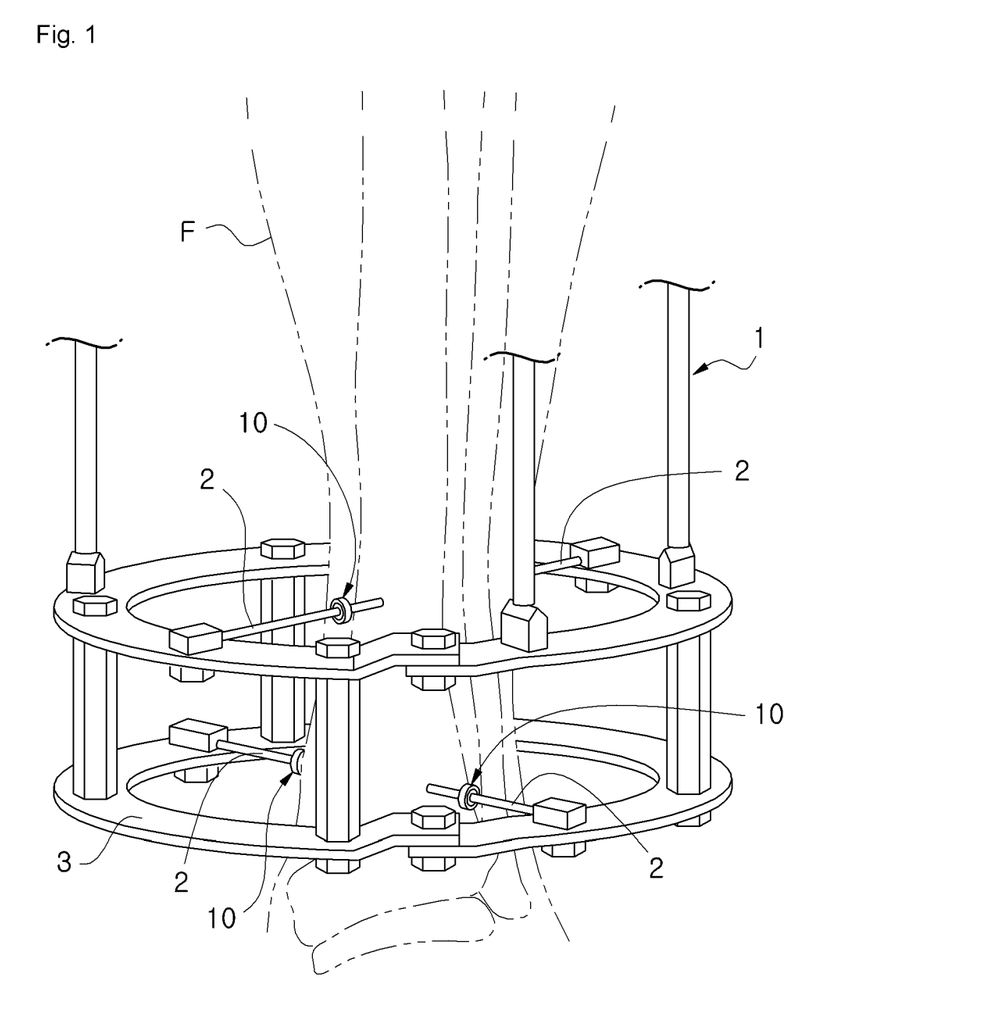
FIG. 1 is a diagram showing the installed condition of a medical wound healing accelerator according to a first embodiment of the present disclosure.
Figure 2:
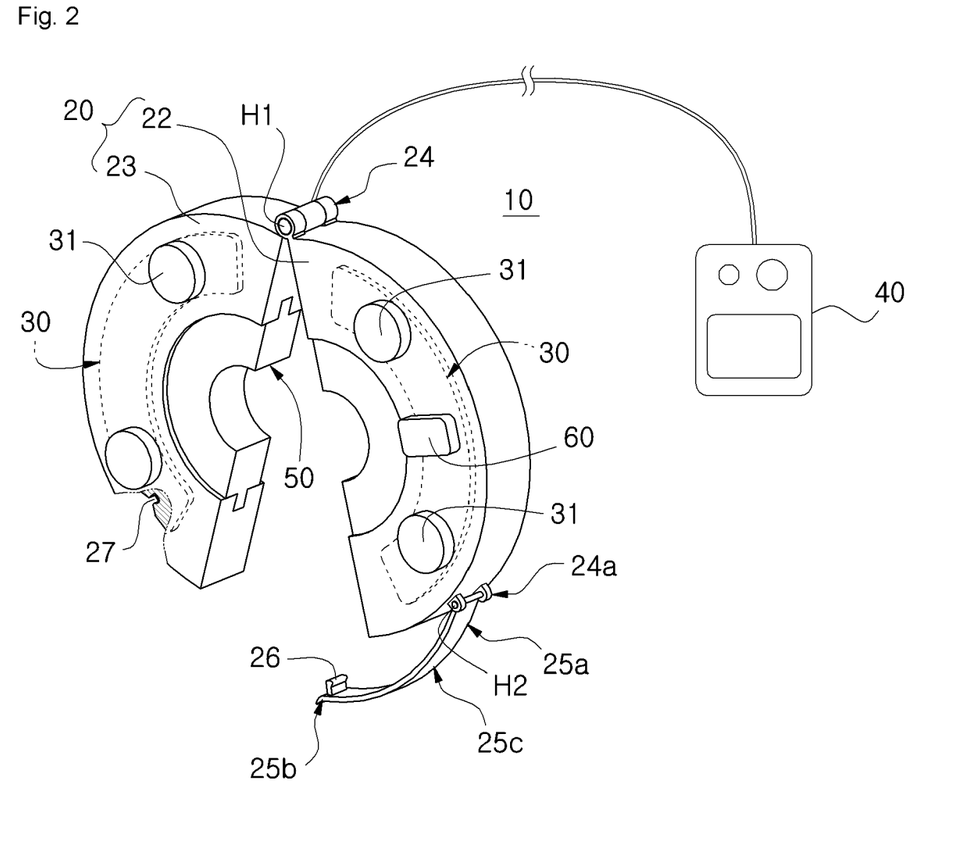
FIG. 2 is a perspective view of a medical wound healing accelerator according to a first embodiment of the present disclosure.
Figure 3:
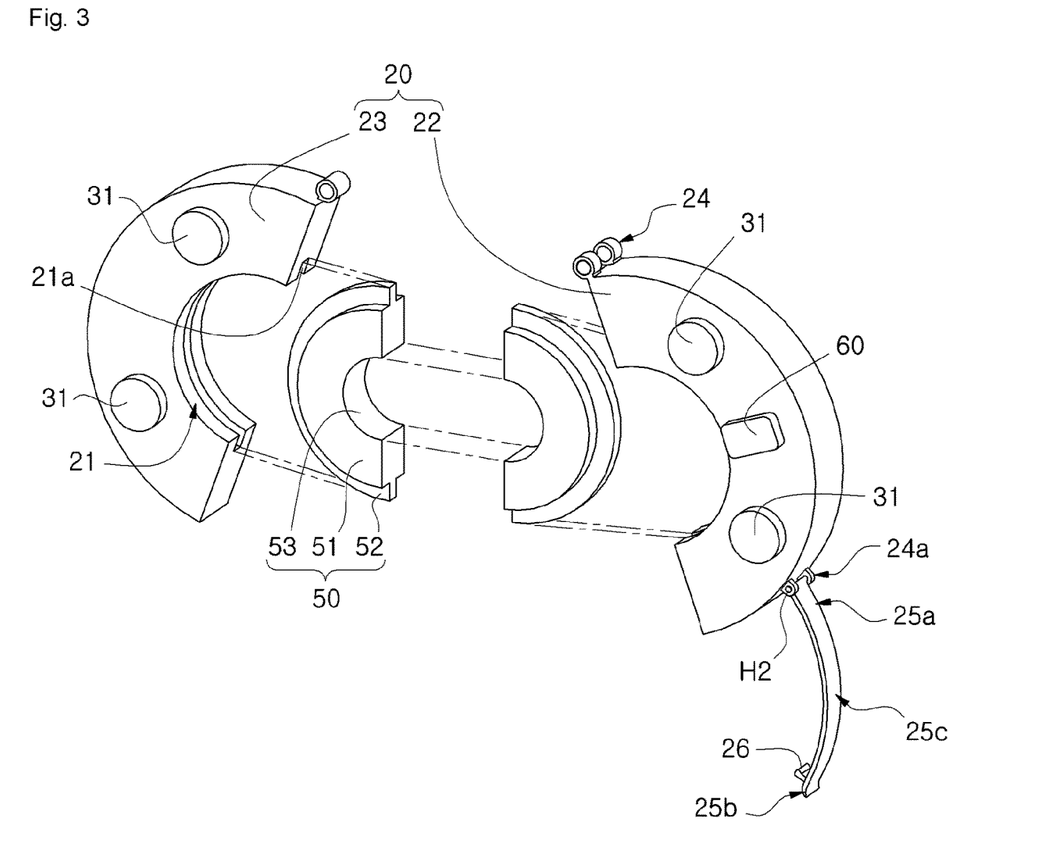
FIG. 3 is an exploded perspective view of a medical wound healing accelerator according to a first embodiment of the present disclosure.

FIG. 1 is a diagram showing the installed condition of a medical wound healing accelerator according to a first embodiment of the present disclosure, FIG. 2 is a perspective view of the medical wound healing accelerator according to the first embodiment of the present disclosure, and FIG. 3 is an exploded perspective view of the medical wound healing accelerator according to the first embodiment of the present disclosure.

Referring to FIGS. 1 to 3, the medical wound healing accelerator 10 according to the first embodiment of the present disclosure includes a body 20, a light source unit 30 and a controller 40.

The body 20 is installed in the external fixator 1 for fracture, and attachably/detachably installed on a fixing pin 2 that is inserted into a bone through the skin F.

The body 20 may be formed in the shape of a circular or polygonal plate, and has an installation hole 21 through which the fixing pin 2 goes at the center, and the body 20 are divided into first and second bodies 22,23 with respect to the vertical center of the installation hole 21.

One side of the first and second bodies 22,23 is hinge coupled through a first hinge 24 such that they can rotate, and the opposite side to the hinge coupled side through the first hinge 24, i.e., the other side is fastened to each other through a fastener 25.

Here, the first hinge 24 interconnects the first and second bodies 22,23, and includes all types of hinges to allow free rotation with respect to a connection point H1.

One side front end of the fastener 25 is rotatably coupled to the outer circumferential surface of the first body 22, and the other side front end is coupled to the outer circumferential surface of the second body 23 by rotation, so that the first and second bodies 22,23 are held together.

The fastener 25 may include various types of fasteners 25, and in the first embodiment of the present disclosure, the fastener 25 may include a coupling end 25a, a fastening end 25b and a connecting end 25c in the shape of a plate.

The coupling end 25a is rotatably hinge coupled to the outer circumferential surface of the first body 22 through a second hinge 24a, and the fastening end 25b is coupled to the outer circumferential surface of the second body 23.

In this instance, the fastening end 25b is inserted into a stoppage groove 27 formed on the outer circumferential surface of the second body 23 through a stoppage step 26 provided at the front end.

Here, the stoppage step 26 may be formed in various shapes such as a ball or a hook.

The connecting end 25c connects the coupling end 25a to the fastening end 25b. In this instance, when the first and second bodies 22,23 are circular, the connecting end 25c has the same curvature as the outer circumferential surface of the first and second bodies 22,23.

Although the foregoing describes that the coupling end 25a of the fastener 25 is coupled to the first body 22 through the second hinge 24a, the present disclosure is not limited thereto, and on the contrary, the coupling end 25a may be coupled to the second body 23 through the second hinge 24a, and the fastening end 25b may be coupled to the first body 22.

By the body 20 provided with the fastener 25, the first and second bodies 22,23 rotate through the connection point H1 of the first hinge 24 to open the installation hole 21, and the opened installation hole 21 is coupled to the outer circumferential surface of the fixing pin 2, so that the first and second bodies 22,23 may be installed on the fixing pin 2.

In this instance, the first and second bodies 22,23 installed on the fixing pin 2 may be fastened and firmly installed on the fixing pin 2 by rotation of the fastener 25 through a connection point H2 of the second hinge 24a.

Meanwhile, a plurality of light source units 30 is arranged on one side surface of the first and second bodies 22,23, to irradiate a beneficial light to a wound i.e., a wound occurring when the fixing pin 2 penetrates the skin F.

The light source unit 30 irradiates blue light having the wavelength between 300 nm and 500 nm using a light emitting diode (LED) 31 as a light source. In this instance, the wavelength of the irradiated blue light preferably has the wavelength between 400 nm and 470 nm.

The blue light having the wavelength between 400 nm and 470 nm provides antibacterial effects and beneficial effects for wound healing acceleration as noted above.

The LED 31 is in the form of a module including a plurality of LEDs mounted on a substrate, and each LED 31 module is received in the first and second bodies 22,23 such that only part of the LED 31 except the substrate is exposed to the outside of the first and second bodies 22,23 to irradiate blue light.

In this instance, the LED 31 module may be received inside through insert molding when fabricating the first and second bodies 22,23, and the first and second bodies 22,23 may be each formed in the shape of a case and received inside (not shown).

That is, the LED 31 module may be received in the first and second bodies 22,23 in various shape or by various methods, and the LED 31 module is well known technology commonly used in the art and its detailed description is omitted herein.

By the light source unit 30 using the LED 31 as a light source, blue light having the wavelength between 400 nm and 470 nm is irradiated through the LED 31 onto regions near a wound occurring when the fixing pin 2 penetrates the skin F.

Accordingly, antibacterial effects and beneficial effects for wound healing acceleration are provided to a wound occurring when the fixing pin 2 penetrates the skin F and regions near the wound, thereby preventing the infection of the skin F and accelerating the wound healing.

The controller 40 is electrically connected to the light source unit 30 to control the operation of the light source unit 30.

The controller 40 is preferably formed in a portable shape, and provides, through an embedded program, on/off function of the light source unit 30 and function to adjust the brightness of the light source unit 30, and timer function to turn on/off the light source unit 30 after a predetermined time passes.

The program embedded in the controller 40 is well known technology commonly used in the art and its detailed description is omitted herein.

Meanwhile, the medical wound healing accelerator 10 according to the first embodiment of the present disclosure may further include an active member 50.

The active member 50 is installed in the installation hole 21 of the body 20 through which the fixing pin 2 goes, and actively responds to the diameter of the fixing pin 2 (see FIG. 3).

That is, the active member 50 is placed between the installation hole 21 of the body 20 and the fixing pin 2, and actively responds to the diameter of the fixing pin 2 having different diameters through shrinkage and restoration.

The active member 50 includes an active body 51 and a coupling flange 52.

The active body 51 has an active hole 53 through which the fixing pin 2 goes at the center, and is divided into half with respect to the vertical center of the active hole 53 such that each is provided in the first and second bodies 22,23.

The coupling flange 52 extends outward along the outer circumferential surface of the active body 51, and is inserted into a coupling groove 21a formed along the inner circumferential surface of the installation hole 21 of the first and second bodies 22,23.

Although the foregoing describes that the active body 51 is divided into half, the present disclosure is not limited thereto, and the active body 51 may be divided into a larger number of parts and installed in the coupling groove 21a at a predetermined interval.

Additionally, the active member 50 may be made of a synthetic resin material having elasticity per se, and a preferable material may include a thermoplastic elastic material or synthetic rubber.

By the active member 50 having elasticity per se, the active hole 53 is interposed between the installation hole 21 of the first and second bodies 22,23 and the fixing pin 2, and may actively respond to the fixing pins 2 having the diameter of various sizes through shrinkage and restoration.

Accordingly, the first and second bodies 22,23 may be easily installed irrespective of the diameter of the fixing pin 2.

Additionally, the active member 50 is supported in close contact with the fixing pin 2 through the elasticity, thereby preventing the slippage of the first and second bodies 22,23 installed on the fixing pin 2, and installing the first and second bodies 22,23 on the fixing pin 2 more firmly.

Meanwhile, the medical wound healing accelerator 10 according to the first embodiment of the present disclosure may further include a light receiving sensor 60.

At least one light receiving sensor 60 is installed on the first and second bodies 22,23 to detect the color of the skin F changing depending on the degree of inflammation, and is electrically connected to the controller 40.

That is, the light receiving sensor 60 transmits information associated with the detected color of the skin F to the controller 40 with the embedded program, and the controller 40 automatically changes the output of blue light irradiated from the light source unit 30 based on the transmitted information.

By the light receiving sensor 60 that detects the color change of the skin F, the output of blue light is automatically adjusted depending on the degree of inflammation, thereby providing high convenience in use to a user of the medical wound healing accelerator 10.

Additionally, as the output of blue light automatically changes depending on the degree of inflammation, high satisfaction and reliability for products may be provided.

Hereinafter, the operation of the medical wound healing accelerator according to the first embodiment of the present disclosure as configured above will be described with reference to FIG. 4.

Figure 4:
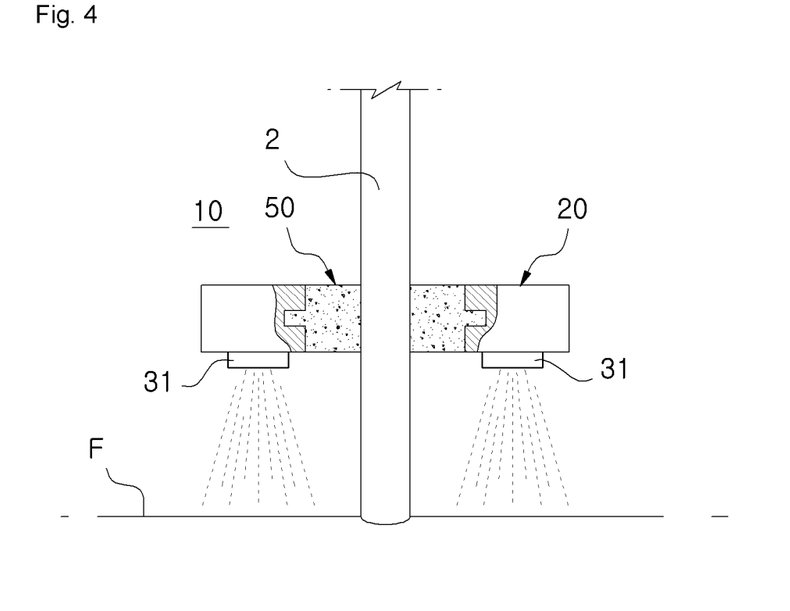
FIG. 4 is a diagram showing the operation of a medical wound healing accelerator according to a first embodiment of the present disclosure.

FIG. 4 is a diagram showing the operation of the medical wound healing accelerator according to the first embodiment of the present disclosure.

Referring to FIG. 4, the medical wound healing accelerator 10 according to the first embodiment of the present disclosure as configured above is installed on the fixing pin 2 that is inserted into the bone through the skin F to irradiate blue light that provides beneficial effects for the skin F.

Accordingly, infection of the skin F caused by the fixing pin 2 penetrating the skin F may be prevented, and healing of a wound occurring when the fixing pin 2 penetrates the skin F may be accelerated.

Additionally, the medical wound healing accelerator 10 according to the first embodiment of the present disclosure is installed on the fixing pin 2 of the external fixator 1 for fracture, thereby easily irradiating blue light onto the skin F without being interrupted by each frame 3 of the external fixator 1 for fracture, and accurately irradiating blue light onto a wound site which through the fixing pin 2 penetrates.

Further, by the medical wound healing accelerator 10 according to the first embodiment of the present disclosure, a patient with fractures using the external fixator 1 for fracture may treat himself/herself without any help of other person, and continuous and consecutive treatment may be achieved.

Hereinafter, a medical wound healing accelerator according to a second embodiment of the present disclosure will be described with reference to FIG. 5.

Figure 5:
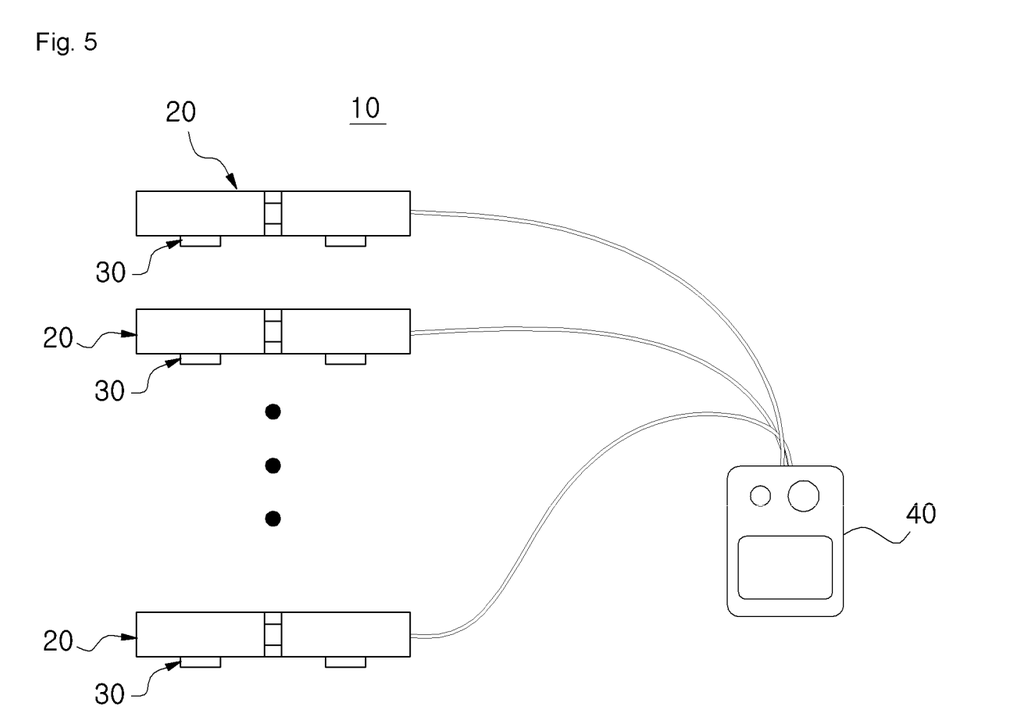
FIG. 5 is a diagram showing the configuration of a medical wound healing accelerator according to a second embodiment of the present disclosure.

FIG. 5 is a diagram showing the configuration of the medical wound healing accelerator according to the second embodiment of the present disclosure.

Referring to FIG. 5, the medical wound healing accelerator 100 according to the second embodiment of the present disclosure has the same configuration and operation as the above-mentioned medical wound healing accelerator 10 of the first embodiment.

However, there is a difference in that one body 20 provided with the light source unit 30 is connected to the controller 40 in the medical wound healing accelerator 10 according to the first embodiment, while a plurality of bodies 20 each provided with the light source unit 30 is electrically connected to one controller 40 in the medical wound healing accelerator 100 according to the second embodiment.

By the medical wound healing accelerator 100 according to the second embodiment of the present disclosure, it is possible to control the plurality of light source units 30 that irradiates blue light through one controller 40, thereby maximizing the convenience of using.

In particular, it is possible to easily respond to each of the plurality of fixing pins 2 installed in the external fixator 1 for fracture.

Hereinafter, an osteomyelitis treatment device according to an embodiment of the present disclosure will be described with reference to FIGS. 6 to 11.

Figure 6:
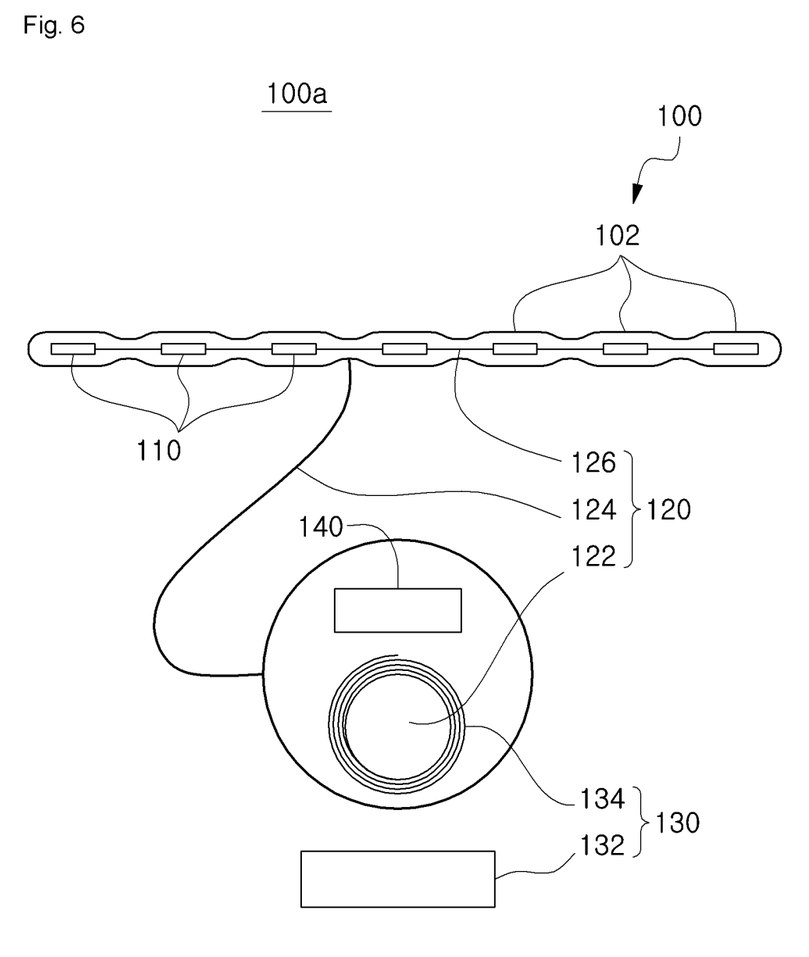
FIG. 6 shows an osteomyelitis treatment device according to a first embodiment of the present disclosure.
Figure 7:
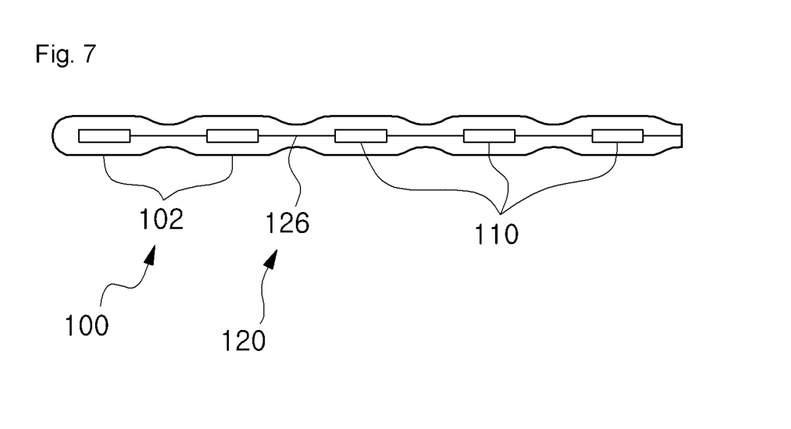
FIGS. 7 and 8 show a cut or folded insert of an osteomyelitis treatment device according to a first embodiment of the present disclosure.
Figure 8:
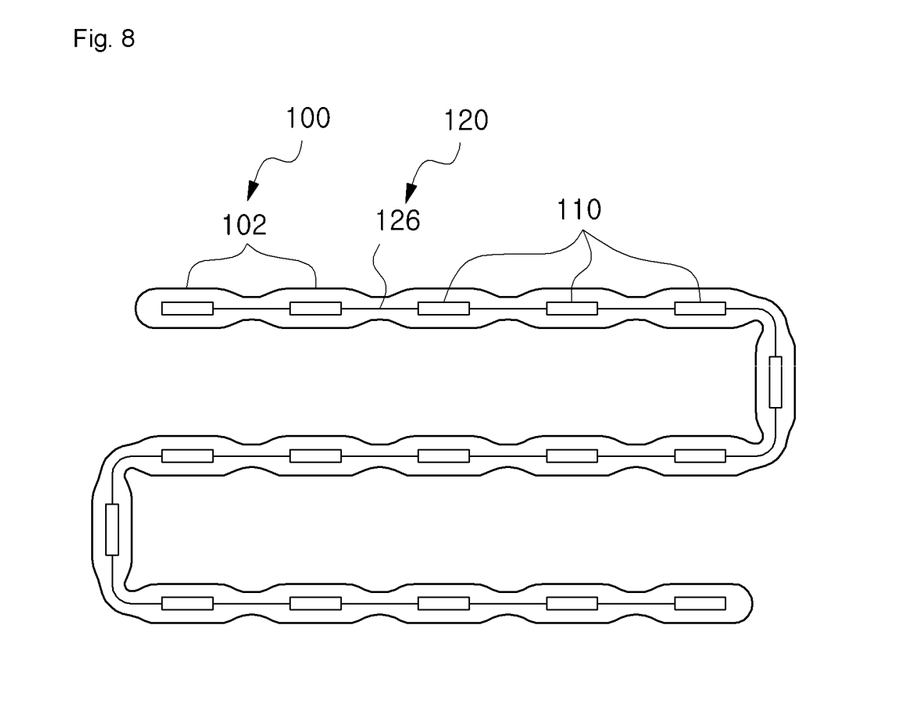
Figure 9:
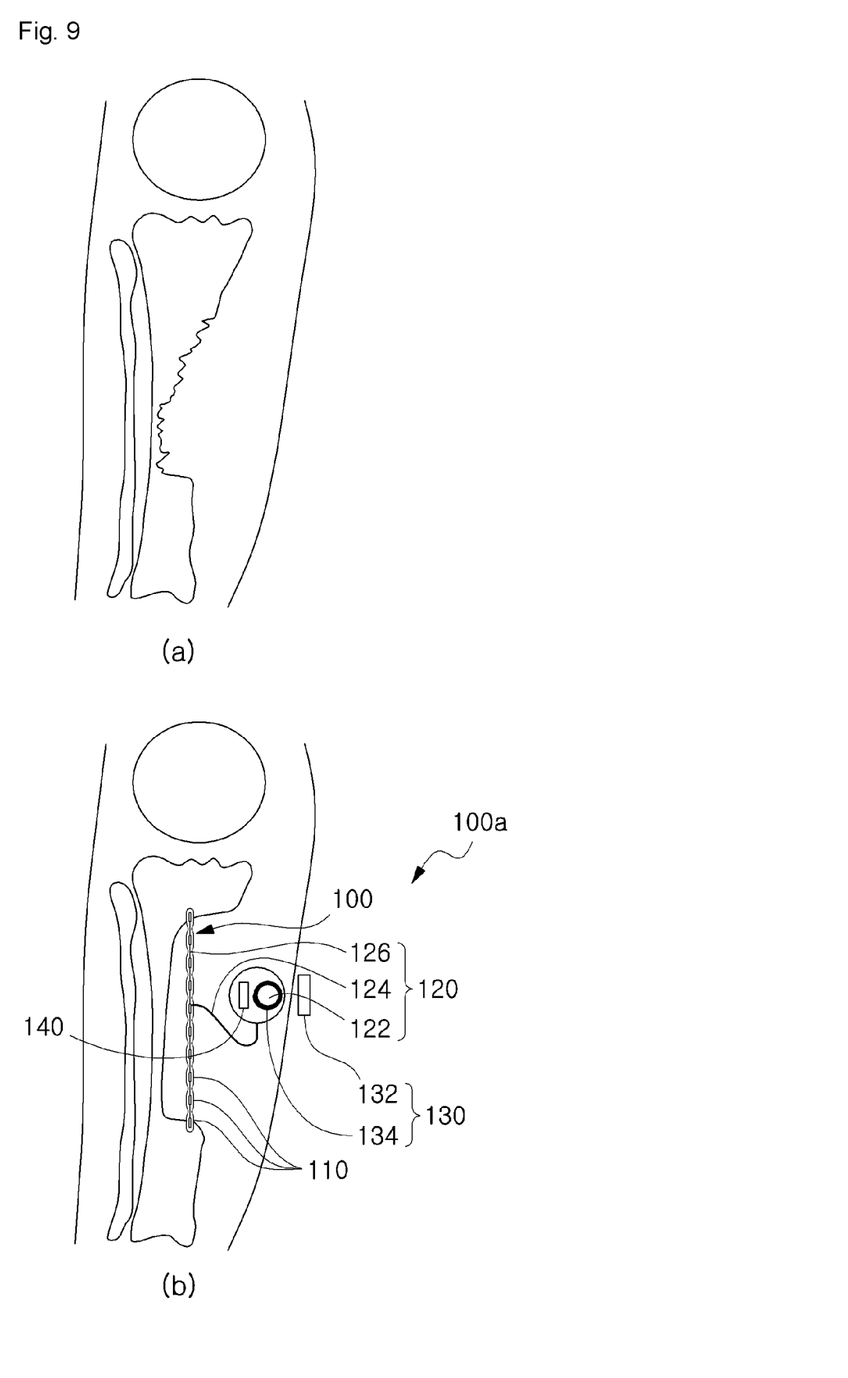
FIG. 9 shows that an osteomyelitis treatment device according to a first embodiment of the present disclosure is placed in an osteomyelitis site.

FIG. 6 shows an osteomyelitis treatment device according to a first embodiment of the present disclosure, FIGS. 7 and 8 shows a cut or folded insert of the osteomyelitis treatment device according to the first embodiment of the present disclosure, and FIG. 9 shows that the osteomyelitis treatment device according to the first embodiment of the present disclosure is placed in an osteomyelitis site.

Referring to FIG. 6, the osteomyelitis treatment device 100a according to the first embodiment of the present disclosure may include an insert 100, a light-emitting member 110, a power supply member 120, a wireless charging member 130 and a controller 140.

The insert 100 may be inserted into, for example, a human body.

For example, the insert 100 may be inserted into osteomyelitis or an osteomyelitis site.

In this instance, the insert 100 may be made of a flexible polymer material, and the exterior of the insert 100 may be coated with silicon of a transparent material harmless for the human body, to form a transparent silicon coating film on the insert 100.

Accordingly, the insert 100 may be easily deformed to conform to the shape of the osteomyelitis site in the human body, and may minimize foreign body reaction in the human body.

Additionally, the insert 100 may be provided with a plurality of receiving blocks 102, and a plurality of light-emitting member 110 may be placed in the plurality of receiving blocks 102.

The plurality of receiving blocks 102 may be connected to each other, and the insert 100 may be cut or folded at the connected part of the plurality of receiving blocks 102.

In relation to this, referring to FIG. 7, in some cases, the insert 100 may be cut. In this instance, the connected part of the plurality of receiving blocks 102 of the insert 100 may be cut. For example, when treatment of a local part in the patient's human body is required or antibacterial action through the light-emitting member 110 is less required, some of the plurality of receiving blocks 102 may be cut to achieve more efficient osteomyelitis treatment.

Meanwhile, referring to FIG. 8, in some cases, the insert 100 may be folded. In this instance, the connected part of the plurality of receiving blocks 102 of the insert 100 may be folded, and accordingly, the elongated insert 100 may be placed in the osteomyelitis site within the human body. For example, when a region required for treatment in the patient's human body is large or antibacterial action through the light-emitting member 110 is greatly required, the plurality of receiving blocks 102 may be folded to achieve more efficient osteomyelitis treatment.

The light-emitting member 110 may be placed in the insert 100.

The light-emitting member 110 may include, for example, an LED that emits blue light. The blue light, for example, blue light of about 470 nm wavelength may have antibacterial action, and may continuously have an antibacterial action while blue light is emitted from the light-emitting member 110.

However, the light-emitting member 110 is not limited thereto, and includes any type of light-emitting member 110 when the light-emitting member 110 may have antibacterial action on the osteomyelitis site in the human body. For example, the light-emitting member 110 may include a laser that emits light with antibacterial action and other phosphors. Additionally, the light-emitting member 110 may include semiconductor crystals of a few nanometers, known as quantum dots, which emit light themselves. The quantum dots gain attention as a next-generation light-emitting device due to higher color purity and optical stability advantages than conventional phosphors.

Additionally, the plurality of light-emitting members 110 may be spaced apart from each other along the lengthwise direction of the insert 100 in the insert 100. In this instance, each light-emitting member 110 may be inserted into each receiving block 102.

As described above, when a low antibacterial effect is necessary, part of the insert 100 may be cut to reduce the number of light-emitting members 110 provided in the insert 100.

Meanwhile, it is obvious that the plurality of light-emitting members 110 provided in the insert 100 may be the same type of light-emitting member or different types of light-emitting members.

The light-emitting member 110 may be connected to the power supply member 120 and the wireless charging member 130.

The power supply member 120 may include a battery 122, a first wire 124, and a second wire 126.

In this instance, the power supply member 120, for example, the battery 122, the first wire 124, and the second wire 126 are preferably made of a biocompatible material because they are inserted into the human body.

The battery 122 may be spaced apart from the insert 100, and may include, for example, a rechargeable battery 122. The first wire 124 may connected between the battery 122 and the insert 100, and the second wire 126 may be connected between the plurality of light-emitting members 110 in the insert 100.

In this instance, because the second wire 126 extends through the parts connecting the plurality of receiving blocks 102 of the insert 100, the second wire 126 may be also cut or folded by cutting or folding of the insert 100.

Although FIG. 6 shows that power supplied from the battery 122 is supplied to the plurality of light-emitting members 110 through connection of the first wire 124 and the second wire 126, a method of supplying power to the plurality of light-emitting members 110 is not limited thereto, and any method that supplies power to the plurality of light-emitting members 110 is available.

Meanwhile, the wireless charging member 130 may charge the battery 122 wirelessly by an electromagnetic induction method.

To this end, the wireless charging member 130 may include an external charger 132 and a charging coil 134.

The external charger 132 may be placed outside of the human body, and may wirelessly charge the battery 122 placed in the human body.

Additionally, the charging coil 134 may be placed adjacent to the battery 122 in the human body, and may generate an induced current by an electromagnetic induction method with the external charger 132.

Because power is continuously supplied to the plurality of light-emitting members 110 by an external battery charging method for charging the battery 122 inserted into human body by the external charger 132, the same antibacterial action may be obtained by the plurality of light-emitting members 110 for a desired period, for example, 6-8 weeks.

Additionally, the controller 140 may be connected to the insert 100 and placed in the human body.

Specifically, the controller 140 may directly/indirectly control the operation of the light-emitting member 110.

For example, the controller 140 may directly transmit an operation signal to the light-emitting member 110 via wired or wireless communication, or indirectly control the operation of the light-emitting member 110 by controlling the operation of the power supply member 120. In this instance, it is obvious that the plurality of light-emitting members 110 may be individually controlled.

Eventually, the controller 140 may adjust various factors such as presence or absence of antibacterial action, antibacterial intensity or cycle of antibacterial action by controlling the operation of the light-emitting member 110.

Referring to FIG. 9, the osteomyelitis treatment device 100a according to the first embodiment is inserted into the human body as below and has an antibacterial action.

For example, the osteomyelitis treatment device 100a according to the first embodiment may be inserted into a tibia osteomyelitis site of the leg, and the tibia osteomyelitis site may be filled with the insert 100. In this instance, the insert 100 may be cut or folded to conform to the size of the tibia osteomyelitis site.

Additionally, the power supply member 120, in particular, the battery 122 may be placed adjacent to the tibia osteomyelitis site, and the insert 110 and the battery 122 may be connected with the first wire 124.

Accordingly, when power is supplied from the power supply member 120 to the light-emitting member 110, the light-emitting member 110 may emit light. In this instance, light emitted from the light-emitting member 110 may have antibacterial action on the tibia osteomyelitis site.

In this instance, because the battery 122 may be wirelessly charged by the external charger 132 of the wireless charging member 130, power may be continuously supplied to the light-emitting member 110. Additionally, because light of the same intensity may be emitted from the light-emitting member 110 while power is supplied to the light-emitting member 110, the same antibacterial effect may be obtained for a long time.

However, the configuration of the power supply member 120 is not limited thereto, and any configuration for supplying power from the power supply member 120 to the light-emitting member 110 is available. For example, it is obvious that the battery 122 may be placed outside of the human body, or power may be directly supplied from the charging coil 134 to the light-emitting member 110 by an electromagnetic induction method without the battery 122.

As described above, the osteomyelitis treatment device 100a according to the first embodiment has the insert made of a polymer material, which makes it easy to fold or cut the insert to conform to the shape of the osteomyelitis site, and the light-emitting member is connected to the battery and the charging coil, allowing wireless charging of the battery, and thus light of the same intensity is emitted from the light-emitting member for a desired period, thereby obtaining the same antibacterial action by the light-emitting member. Additionally, it is possible to effectively prevent or treat osteomyelitis by the light-emitting member for blue light, and allow local site irradiation in the human body by the light-emitting member, thereby preventing systemic complications.

The osteomyelitis treatment device 100a according to the first embodiment has been hereinabove described, and an osteomyelitis treatment device 200a according to a second embodiment will be described as below.

Figure 10:
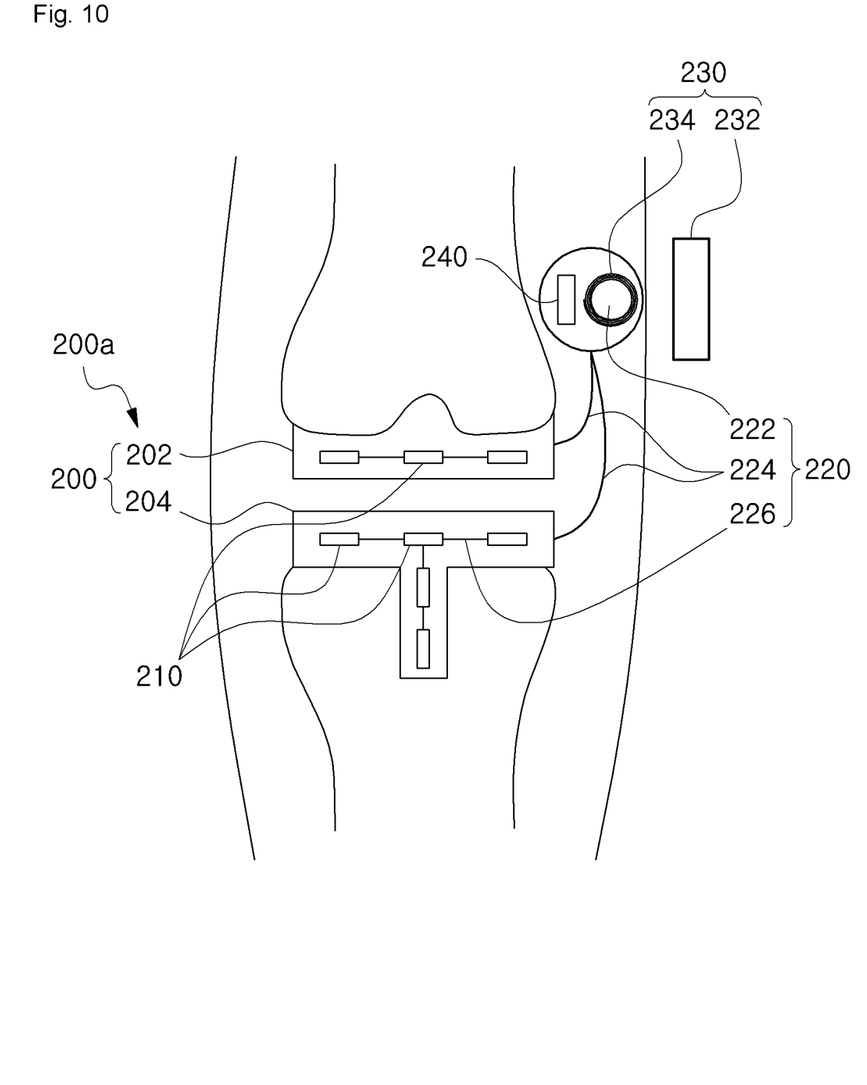
FIG. 10 shows an osteomyelitis treatment device according to a second embodiment of the present disclosure.

FIG. 10 shows the osteomyelitis treatment device according to the second embodiment of the present disclosure.

Referring to FIG. 10, the osteomyelitis treatment device 200a according to the second embodiment of the present disclosure may include an insert 200, a light-emitting member 210, a power supply member 220, a wireless charging member 230 and a controller 240.

The insert 200, the light-emitting member 210, the power supply member 220, the wireless charging member 230 and the controller 240 correspond to the insert 100, the light-emitting member 110, the power supply member 120, the wireless charging member 130 and the controller 140 described in the above-mentioned osteomyelitis treatment device 100a according to the first embodiment, and the following description is primarily based on a difference between the osteomyelitis treatment device 100a according to the first embodiment and the osteomyelitis treatment device 200a according to the second embodiment.

For example, when artificial joint is infected after artificial joint surgery, the osteomyelitis treatment device 200a according to the second embodiment may be inserted into the human body after removal of the infected artificial joint, and may be designed suitably for artificial joint infection treatment.

The insert 200 may include a first insert 202 and a second insert 204.

For example, the first insert 202 may be connected to the end of femur, the second insert 204 may be connected to the end of tibia, and the first insert 202 and the second insert 204 may be placed facing each other.

In this instance, the first insert 202 and the second insert 204 may have different shapes depending on the shape of the end of femur and the end of tibia.

Additionally, the first insert 202 and the second insert 204 may be made of a polymer material, and may be fabricated with a desired shape and size by 3D printing technology.

For example, the shape or size of the end of femur and the end of tibia may differ each patient, and the insert 200 may be customized for each patient by applying 3D printing technology.

The light-emitting member 210 may be inserted into the insert 200 fabricated as above.

For example, the plurality of light-emitting members 210 may be spaced apart from each other in the first insert 202 and the second insert 204, and the number of light-emitting members 210 inserted into the first insert 202 and the second insert 204 may differ.

Meanwhile, the power supply member 220 may be spaced apart from the first insert 202 and the second insert 204.

The power supply member 220 may include a battery 222, a first wire 224 and a second wire 226.

The battery 222 may be placed on one side in the knee.

The first wire 224 may be connected from the battery 222 to each of the first insert 202 and the second insert 204. Accordingly, the first wire 224 may simultaneously supply power from the battery 222 to the light-emitting member 210 inserted into the first insert 202 and the light-emitting member 210 inserted into the second insert 204.

The second wire 226 may be placed in each of the first insert 202 and the second insert 204, and may connect the plurality of light-emitting members 210 inserted into the first insert 202, and connect the plurality of light-emitting members 210 inserted into the second insert 204.

Additionally, the wireless charging member 230 may include an external charger 232 placed outside of the human body and a charging coil 234 placed adjacent to the battery 222, and may wirelessly charge the battery 222 by an electromagnetic induction method.

Finally, the operation of the light-emitting member 210 or the power supply member 220 may be controlled by the controller 240. Accordingly, the antibacterial action of the light-emitting member 210 may be controlled.

As described above, the osteomyelitis treatment device 200a according to the second embodiment may easily fabricate the insert to conform to the shape of the patient's osteomyelitis site or joint or with customized shape and size desired by the patient using 3D printing fabrication technology, and further, may be used to treat osteomyelitis of tibia as well as deep soft tissue infection, osteomyelitis, and infection in artificial joint inserted sites of all parts of the body including the knees, such as hip joints, shoulder joints and knee joints.

The osteomyelitis treatment device 200a according to the second embodiment has been hereinabove described, and an osteomyelitis treatment device 300a according to a third embodiment is described below.

Figure 11:
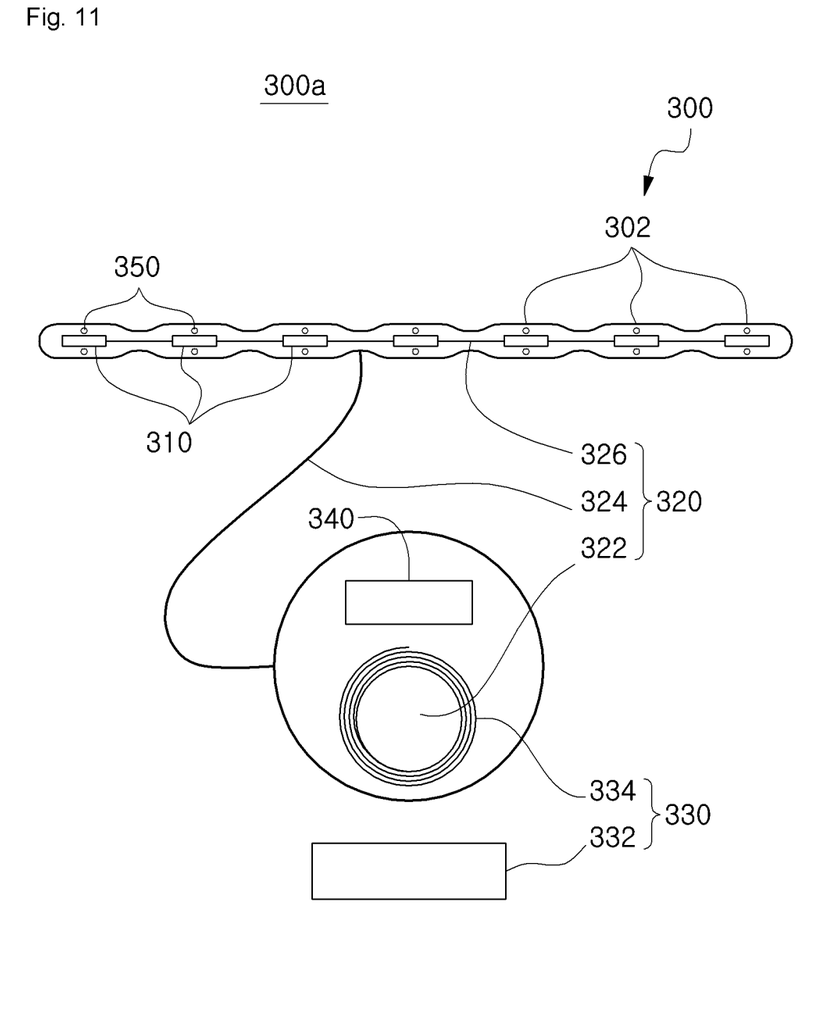
FIG. 11 shows an osteomyelitis treatment device according to a third embodiment of the present disclosure.

FIG. 11 shows the osteomyelitis treatment device according to the third embodiment of the present disclosure.

Referring to FIG. 11, the osteomyelitis treatment device 300a according to the third embodiment may include an insert 300, a light-emitting member 310, a power supply member 320, a wireless charging member 330, a controller 340 and a capsule 350.

The insert 300, the light-emitting member 310, the power supply member 320, the wireless charging member 330 and the controller 340 are components corresponding to the insert 100, the light-emitting member 110, the power supply member 120, the wireless charging member 130 and the controller 140 of the osteomyelitis treatment device 100a according to the first embodiment, and a description of the insert 300, the light-emitting member 310, the power supply member 320, the wireless charging member 330 and the controller 340 is omitted herein.

The insert 300 may be provided with a capsule 350.

The capsule 350 may receive an antibacterial material or a pain mitigation material therein, and when the capsule 350 is broken, the antibacterial material or pain mitigation material received in the capsule 350 may be discharged outwards.

In this instance, the capsule 350 may be broken by light emitted from the light-emitting member 310 or an external environment around the osteomyelitis site.

For example, the capsule 350 may be broken by light emitted from the light-emitting member 310. The capsule 350 may be artificially broken by the wavelength of light and the intensity of light emitted from the light-emitting member 310, or a temperature change caused by light emitted from the light-emitting member 310.

In this instance, whether the capsule 350 is broken or not is determined by controlling the operation of the light-emitting member 310, thereby controlling the antibacterial action or pain mitigation action by the capsule 350.

Additionally, the capsule 350 may be designed to break in the specific condition of external environment such as specific temperature range, specific pressure range and specific humidity range, and when the external environment around the osteomyelitis site reaches such condition, the capsule 350 may be broken itself. However, the external environment condition for the breakage of the capsule 350 is not limited thereto, and any condition affecting the breakage of the capsule 350 is available.

As described above, the osteomyelitis treatment device 300a according to the third embodiment further includes the capsule in the insert, thereby obtaining more effective antibacterial effects through individual antibacterial action of the light-emitting member and the capsule or antibacterial action by interaction between the capsule and the light-emitting member. For example, when it is necessary to obtain a great antibacterial effect due to a large degree of bone infection, a great antibacterial effect may be obtained more quickly by simultaneously using the capsule and the light-emitting member.

While various embodiments of the present disclosure have been hereinabove described, the present disclosure is not limited to the above embodiments, and includes the full range of modifications that are easily made by those skilled in the art from the embodiments of the present disclosure and accepted equivalent.

The invention claimed is:

1. A medical wound healing accelerator, comprising:
   a body configured to be removably installed on a fixing pin of an external fixator for fracture, the fixing pin configured to be fixed to a bone through a wound site on skin, and the body comprising a through hole for receiving the fixing pin, the through hole extending between a bottom surface of the body and a top surface of the body, wherein the body is divided into a first body and a second body, and the first body and the second body are coupled to each other on a first side of the body via a first hinge, and are fastened to each other through a fastener provided on a second side of the body;
   wherein a coupling end of the fastener is rotatably coupled to an outer circumferential surface of the first body via a second hinge, and a fastening end of the fastener is removably coupled to an outer circumferential surface of the second body so the first body and the second body are fastened to each other;
   a plurality of light source units arranged on the bottom surface of the body and oriented to irradiate a blue light toward the fixing pin;
   wherein irradiation of the blue light provides an antibacterial effect;
   a controller electrically connected to the light source units to control operation of the light source units; and
   at least one light receiving sensor installed on the body and electrically connected to the controller;
   wherein the light receiving sensor detects a change in wound site skin color at penetration site of the fixing pin depending on a degree of inflammation, wherein the change in skin color is an increase in redness due to inflammation, and transmits information associated with the detected change in skin color depending on the degree inflammation to the controller, and wherein the controller adjusts output of blue light irradiated from the light source unit based on the detected change in skin color depending on the degree of inflammation;
   the medical wound healing accelerator further comprising an active member configured to be installed in an inner circumferential surface of the through hole of the body to adjust a diameter of the through hole relative to a diameter of the fixing pin;

wherein the active member comprises:
an active body having an active hole through which the fixing pin goes; and
a coupling flange extending outward along an outer circumferential surface of the active body and protruding in an annular shape having a predetermined thickness, the coupling flange configured to be inserted into a coupling hole formed along the inner circumferential surface of the through hole formed in the body and recessed in an annular shape having a predetermined thickness.

2. The medical wound healing accelerator according to claim 1, wherein the fastener includes:
a coupling end rotatably coupled to an outer circumferential surface of the first body;
the fastening end fastened to an outer circumferential surface of the second body; and
a connecting end connecting the coupling end to the fastening end.

3. The medical wound healing accelerator according to claim 1, wherein each of the plurality of light source units irradiates blue light of 300 nm to 500 nm wavelength using a light emitting diode (LED) as a light source.

4. The medical wound healing accelerator according to claim 1, wherein the active member is made of a synthetic resin material having elasticity per se.

5. A medical wound healing accelerator, comprising:
a plurality of bodies, wherein each body of the plurality of bodies is:
configured to be removably installed on a fixing pin of an external fixator for fracture, the fixing pin configured to be fixed to a bone through a wound site on skin,
independent and separate from other bodies in the plurality of bodies,
configured to be coupled together and form a through hole extending from a bottom surface to a top surface of the coupled plurality of bodies, and
divided into a first body and a second body, wherein the first body and the second body are coupled to each other on a first side of the body via a first hinge, and are fastened to each other through a fastener provided on a second side of the body;
wherein a coupling end of the fastener is rotatably coupled to an outer circumferential surface of the first body via a second hinge, and a fastening end of the fastener is fastened to an outer circumferential surface of the second body so the first body and the second body are fastened to each other;
a plurality of light source units arranged on a bottom surface of each body of the plurality of bodies to irradiate a blue light toward the fixing pin;
wherein irradiation of the blue light provides an antibacterial effect;
a controller electrically connected to each of the plurality of light source units installed in each body of the plurality of bodies to control operation of the light source units; and
at least one light receiving sensor installed on the body and electrically connected to the controller;
wherein the light receiving sensor detects a change in wound site skin color at penetration site of the fixing pin depending on a degree of inflammation, wherein the change in skin color is an increase in redness due to inflammation, and transmits information associated with the detected change in skin color depending on the degree inflammation to the controller, and wherein the controller adjusts output of blue light irradiated from the light source unit based on the detected change in skin color depending on the degree of inflammation;
the medical wound healing accelerator further comprising an active member configured to be installed in an inner circumferential surface of the through hole of the body to adjust a diameter of the through hole relative to a diameter of the fixing pin;
wherein the active member comprises:
an active body having an active hole through which the fixing pin goes; and
a coupling flange extending outward along an outer circumferential surface of the active body and protruding in an annular shape having a predetermined thickness, the coupling flange configured to be inserted into a coupling hole formed along the inner circumferential surface of the through hole formed in the body and recessed in an annular shape having a predetermined thickness.

6. The medical wound healing accelerator according to claim 5, wherein the fastener comprises:
the coupling end rotatably coupled to the outer circumferential surface of the first body;
the fastening end fastened to the outer circumferential surface of the second body; and
a connecting end connecting the coupling end to the fastening end.

7. The medical wound healing accelerator according to claim 5, wherein each of the plurality of light source units irradiates blue light of 300 nm to 500 nm wavelength using a light emitting diode (LED) as a light source.

* * * * *